United States Patent [19]

Justice et al.

[11] 4,318,301

[45] Mar. 9, 1982

[54] APPARATUS FOR MEASURING PAPILLARY MUSCLE CONTRACTILITY

[75] Inventors: Richard E. Justice, Gloucester; Gene A. Grindlinger, Brookline; Herbert B. Hechtman, Chestnut Hill, all of Mass.

[73] Assignee: President and Fellows of Harvard College, Cambridge, Mass.

[21] Appl. No.: 162,191

[22] Filed: Jun. 23, 1980

[51] Int. Cl.³ .................... A61N 1/00; A61B 10/00
[52] U.S. Cl. ................................ 73/432 R; 128/783
[58] Field of Search ............ 73/379, 432 R; 128/749, 128/783

[56] References Cited

PUBLICATIONS

Phipps & Bird, Inc., Isolated Organ/Tissue Bath, 7053-400 (1976).
Ugo Basile, Isolated Organ Baths, prior to 1980.
Yeatman et al., Amer. J. Physiology, vol. 220 (2), 534-542 (1971).
Kelly et al., Am. J. Physiol., vol. 199 (1), 157-162 (1960).
Jewell et al., J. Physiol., vol. 235, 715-740 (1973).
Ullrick, Am. J. Physiol., vol. 206 (6), 1285-1290 (1964).

*Primary Examiner*—James J. Gill

[57] ABSTRACT

Apparatus for measuring papillary muscle contractility when subjected to electrical stimulus while immersed in a test bathing liquid includes a test chamber for maintaining the liquid at a controlled temperature and having a membrane for diffusion of oxygen into the liquid, arms for mounting a muscle specimen in the liquid, electrodes for providing an electrical stimulus, and a system for measuring the contractile response of the muscle when subjected to electrical stimulus.

4 Claims, 6 Drawing Figures

APPARATUS FOR MEASURING PAPILLARY MUSCLE CONTRACTILITY

The invention described herein was made in the course of work under a grant or award from the Department of Health, Education and Welfare.

This invention relates to apparatus for measuring papillary muscle contractility when subjected to electrical stimulus while immersed in a bathing liquid such as plasma or an aqueous polyelectrolyte solution and pertains more specifically to apparatus which operates with a very small volume of bathing liquid of the order of 4-10 ml or less.

The tension developed by a papillary muscle mounted in an in vitro chamber has become a standard method for the measure of isometric contractility. The standard method uses a relatively large volume (of the order of 100 ml or more) of an aqueous polyelectrolyte solution for bathing the muscle specimen. Oxygen and carbon dioxide levels in the solution are maintained by bubbling gas into the solution through a sintered plate and the temperature is regulated by pumping the solution through a heat exchanger. Electrodes immersed in the polyelectrolyte solution provided an electrical stimulus for the muscle specimen and the contractile effect is measured by suitable instrumentation. Such a system has been used to evaluate the effect of various materials dissolved or dispersed in the polyelectrolyte solution.

For certain diagnostic work and in order to predict the effect of drugs on hearts under various conditions, it would be desirable to employ a specimen of human plasma as the liquid in which the specimen of animal papillary muscle is bathed or immersed. Not only does the large volume of liquid required by systems previously known militate against the use of plasma but, in addition, the bubbling of oxygen and/or other gases as well as the necessary stirring or agitation of the plasma specimen causes excessive foaming and mechanical distortions of the muscle specimen, preventing an accurate measurement of muscle tension.

The present invention provides apparatus for measuring papillary muscle contractility which overcomes these difficulties. More particularly, the invention provides apparatus for measuring papillary muscle contractility when subjected to electrical stimulus while immersed in a bathing liquid such as plasma or aqueous polyelectrolyte solution which comprises a first chamber for containing test bathing liquid, means for mounting a papillary muscle specimen in fixed location within said chamber in said bathing liquid, a pair of spaced apart electrodes mounted within said chamber at opposite sides of said location to apply an electrical stimulus to said specimen, means for controlling the temperature of said test bathing liquid, means for oxygenating said test bathing liquid comprising a second chamber adjacent the first adapted to contain a supply of oxygen gas, and a membrane permeable to gaseous oxygen and impermeable to said test bathing liquid, said membrane being mounted between said first and second chambers with one face arranged to contact said bathing liquid and the opposite face arranged to contact said gaseous oxygen, and means for measuring the contractible response of said muscle specimen when subjected to electrical shock.

A preferred embodiment of the invention is illustrated in the accompanying drawings, in which FIG. 1 is an isometric view, partly broken away and in section showing a test chamber;

Figure 1:
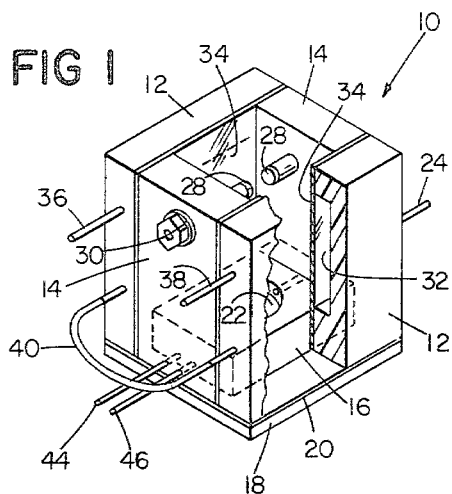

In the embodiment shown in the drawings, test chamber 10 is in the form of a rectangular open topped container having side walls 12, 12 and end walls 14, 14 of a rigid plastic material such as polymethylmethacrylate mounted on a metallic base 16, all secured together in liquid tight relation and mounted on a rigid plastic bottom plate 18 with an interposed sealing gasket 20, all forming a unitary chamber. Metal base 16 is preferably composed of a non-magnetic metal such as aluminum and is provided with a central well 22 in its upper face with which communicates tube 24 extending through end wall 14 to serve as an inlet and outlet for the liquid within the chamber, the total capacity of the chamber being of the order of 4-10 ml. The surface of base 16 and well 22 in contact with the liquid in the chamber is preferably coated with an inert plastic composition such as polytetrafluoroethylene. Loosely disposed within well 22 is an iron stirring rod 26 also coated with the same inert plastic. Spaced apart stainless steel electrodes 28, 28 are mounted on insulated pin jacks 30, 30 threaded in tapped openings in end walls 14, 14. By rotation of jacks 30, the position of electrodes 28 can be adjusted toward and away from each other and toward and away from the fixed location of the papillary muscle specimen as will be explained below.

Each of side walls 12, 12 is provided with a chamber 32 separated from the central or main chamber 10 containing the bathing liquid by a membrane 34 permeable to gases such as oxygen and carbon dioxide but impermeable to aqueous liquids. A suitable membrane is formed of reinforced silicone rubber approximately 0.178 ml thick bonded in place with a suitable silicone adhesive. Inlet and outlet ports 36, 38 together with connecting passage 40 permit the continuous flow of a gas mixture such as one containing 95% oxygen and 5% carbon dioxide through chambers 32.

A cavity 42 in the bottom of metal base 16 is provided with inlet and outlet ports 44, 46 through which a supply of temperature control liquid is circulated to maintain the temperature of the contents of chamber 10 at the desired level.

Chamber 10 is removably positioned on top of support housing 48, which is preferably of rigid plastic material, within which is mounted a rotatable permanent magnet 50 driven by electric motor 52. Magnet 50 is positioned sufficiently close to stirring rod 26 so that the two are magnetically coupled in the usual manner, the stirring rod being rotated as the magnet is rotated.

Figure 2:
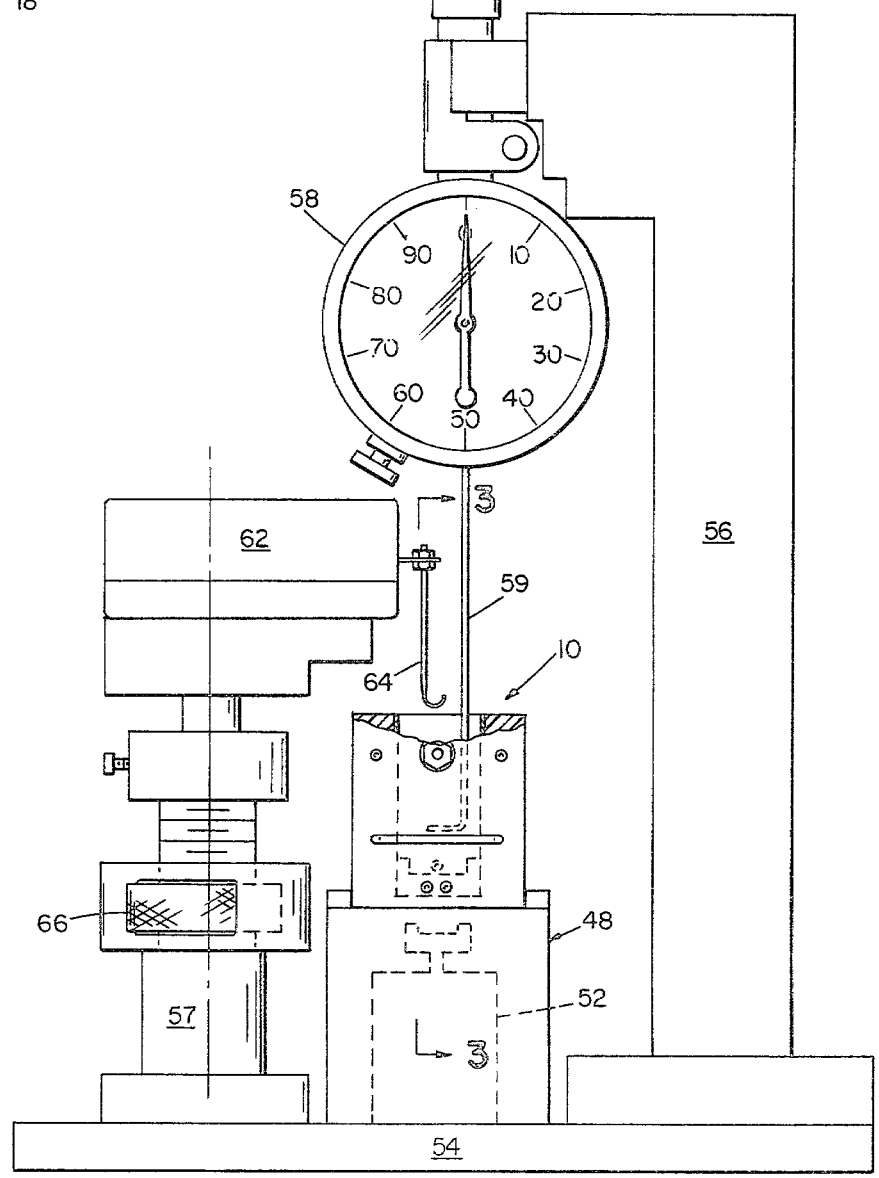
FIG. 2 is a view in side elevation showing the test chamber together with a magnetic stirrer driver, a force transducer, and a micrometer for mounting the muscle specimen.
Figure 3:
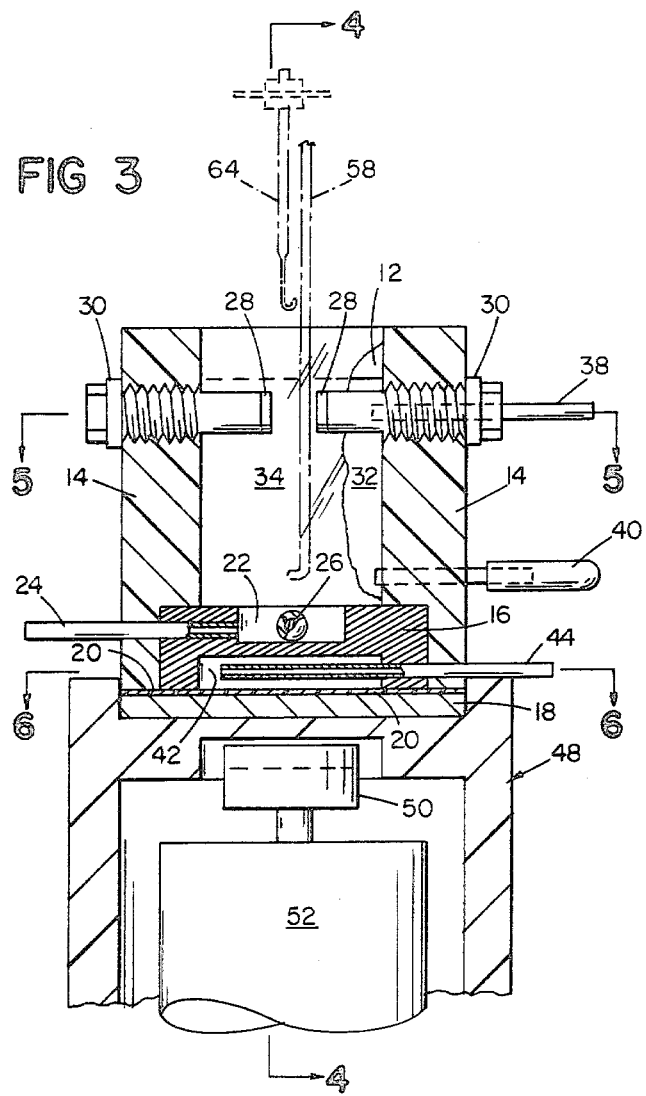
FIG. 3 is a view in section partly broken away taken along line 3—3 of FIG. 2.
Figure 4:
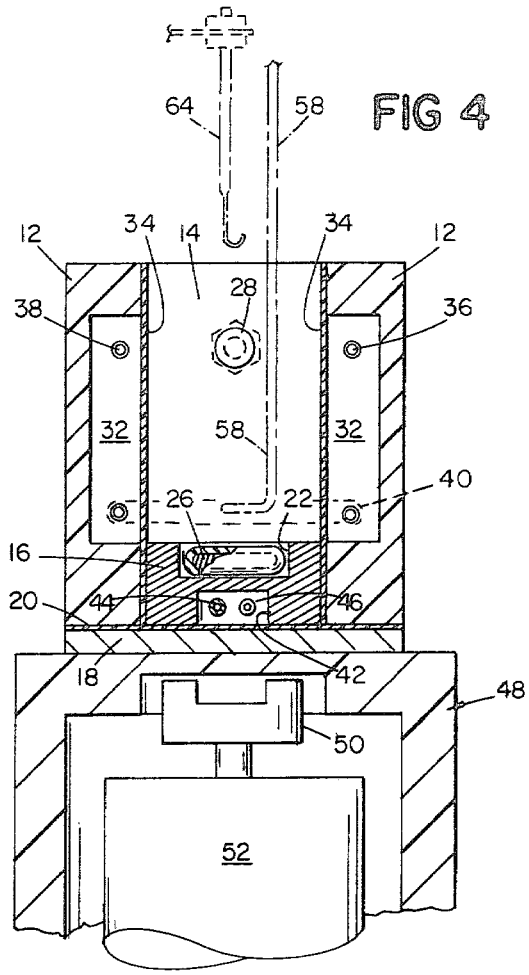
FIG. 4 is a view in section taken along line 4—4 of FIG. 3.
Figure 5:
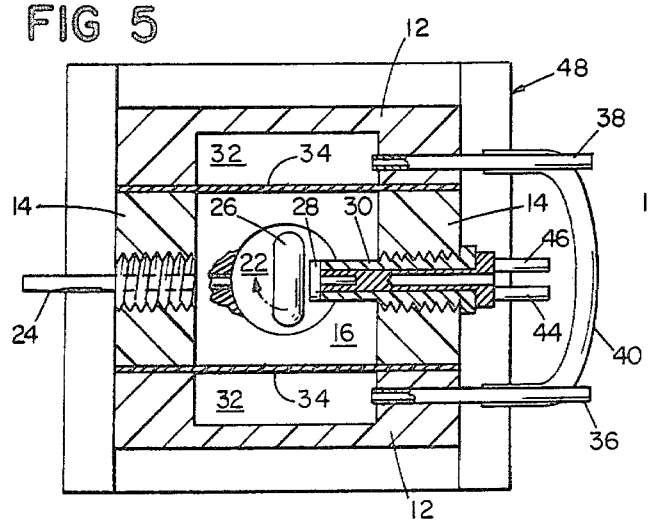
FIG. 5 is a view in horizontal section taken along line 5—5 of FIG. 3.
Figure 6:
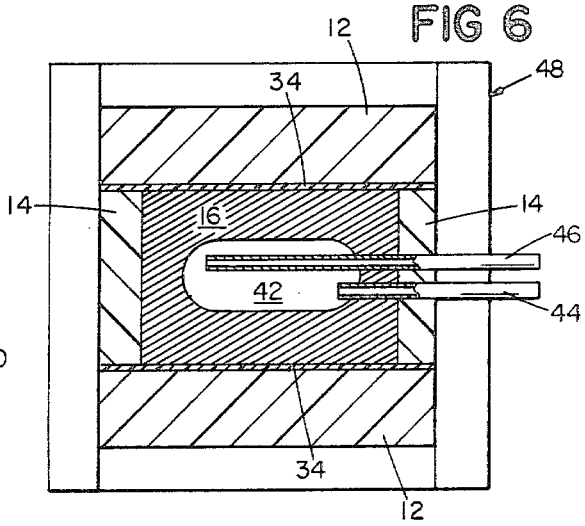
FIG. 6 is a view in horizontal section taken along line 6—6 of FIG. 3.

Support housing 48 is fixed to base 54 (FIG. 2) along with micrometer support column 56 and force transducer support column 57. Micrometer 58 together with specimen mounting arm 59 of stainless steel or other non-magnetic material is threadedly mounted on the upper end of support column 56 and may be vertically adjusted to vary the position of the lower end of mounting arm 59 by rotation of knurled adjustment 60. Force transducer 62 carrying specimen mounting arm 64 is also threadedly mounted on its supporting column 54 vertical adjustment by means of knurled nut 66. Transducer 62 is also rotatable about the vertical axis of column 57 to facilitate insertion and removal of the muscle specimen.

In operation of the device, a specimen of papillary muscle from an animal such as a rat is mounted between the ends of mounting arm 59 and 64 by means of stainless steel spiral spring clips so that it is retained in the desired fixed location. Sufficient specimen of plasma or other desired test solution is introduced into chamber 10 to bath or immerse the muscle specimen, the flow of temperature control liquid through cavity 42 along with rotation of stirring rod 26 is continued until the liquid sample and muscle specimen have attained the desired temperature, and the flow of gas (usually a mixture of 95% oxygen and 5% carbon dioxide) is continued through chambers 32 to maintain the desired gas tension in the bathing liquid (e.g., 500 mm Hg oxygen and 35 mm Hg carbon dioxide). When equilibrium has been achieved, the initial tension on the muscle specimen is adjusted to the desired value by vertical adjustment of micrometer 56 or transducer 62 or both, the electrodes are positioned at the desired spacing at opposite sides of the muscle specimen, and an electrical stimulus is provided through electrodes 28, 28. The stimulating voltage is set just above threshold and is delivered as a 4.5 msec square-wave pulse once every 5 seconds. The signal output of the force transducer can be displayed in any suitable manner as on an oscilloscope or a digital voltmeter or a rapid responding recorder.

No foaming of the plasma or other liquid occurs, and temperature is readily controlled to I 0.5° C. within the range of 20°–40° C. using a flow of water through cavity 42 at the rate of 40–100 ml/min. when the thickness of the aluminum web separating cavity 42 from well 22 is 2 mm and the plastic coating on the inner surface of base 16 is 0.004 mm thick.

What is claimed is:

1. Apparatus for measuring papillary muscle contractility when subjected to electrical stimulus while immersed in a bathing liquid such as plasma or aqueous polyelectrolyte solution which comprises a first chamber for containing test bathing liquid, means for mounting a papillary muscle specimen in fixed location within said chamber in said bathing liquid, a pair of spaced apart electrodes mounted within said chamber at opposite sides of said location to apply an electrical stimulus to said specimen, means for controlling the temperature of said test bathing liquid, means for oxygenating said test bathing liquid comprising a second chamber adjacent the first adapted to contain a supply of oxygen gas, and a membrane permeable to gaseous oxygen and impermeable to said test bathing liquid, said membrane being mounted between said first and second chambers with one face arranged to contact said bathing liquid and the opposite face arranged to contact said gaseous oxygen, and means for measuring the contractible response of said muscle specimen when subjected to electrical shock.

2. Apparatus as claimed in claim 1 in which said membrane is silicone rubber.

3. Apparatus as claimed in claim 1 in which said means for measuring contractile response includes means for adjusting the mounting means to vary the initial tension of said papillary muscle specimen and means for measuring the increase in force produced by said electrical stimulus.

4. Apparatus as claimed in claim 1 in which said membrane forms a portion of the wall of said first chamber.

* * * * *